United States Patent
Posner et al.

(10) Patent No.: US 12,268,636 B2
(45) Date of Patent: Apr. 8, 2025

(54) CORNEAL LINEAR AXIS MARKER

(71) Applicant: Posner Ophthalmic Consultants LLC, Merion Station, PA (US)

(72) Inventors: Michael Posner, Merion Station, PA (US); Matthew Dykes, Magnolia, TX (US); Ronald Dykes, The Woodlands, TX (US)

(73) Assignee: Posner Ophthalmic Consultants LLC, Merion Station (PA)

( * ) Notice: Subject to any disclaimer, the term of this patent is extended or adjusted under 35 U.S.C. 154(b) by 0 days.

(21) Appl. No.: 18/422,448

(22) Filed: Jan. 25, 2024

(65) Prior Publication Data

US 2024/0156640 A1    May 16, 2024

Related U.S. Application Data

(63) Continuation of application No. 17/384,249, filed on Jul. 23, 2021, now Pat. No. 11,911,316.

(60) Provisional application No. 63/055,755, filed on Jul. 23, 2020.

(51) Int. Cl.
*A61F 9/013*    (2006.01)

(52) U.S. Cl.
CPC .................. *A61F 9/0136* (2013.01)

(58) Field of Classification Search
CPC .. A61F 9/013; A61F 9/007; A61F 9/00–0136; A61B 90/39–2090/3995
See application file for complete search history.

(56) References Cited

U.S. PATENT DOCUMENTS

| | | | |
|---|---|---|---|
| 4,357,941 A * | 11/1982 | Golubkov | A61F 9/0136 606/166 |
| 4,526,171 A | 7/1985 | Schachar | |
| 4,665,914 A | 5/1987 | Tanne | |
| 4,739,761 A | 4/1988 | Grandon | |
| 4,907,587 A * | 3/1990 | Fedorov | A61F 9/013 128/897 |
| 5,531,753 A | 7/1996 | Oliveira | |
| 5,618,292 A * | 4/1997 | Poler | A61F 9/0136 606/166 |
| 5,653,723 A | 8/1997 | Kamerling et al. | |
| 5,752,967 A | 5/1998 | Kritzinger et al. | |
| 5,934,285 A * | 8/1999 | Kritzinger | A61F 9/00804 606/166 |
| 6,217,596 B1 * | 4/2001 | Farah | A61F 9/0136 606/166 |
| 9,011,470 B2 | 4/2015 | Mackool | |
| 9,283,117 B2 | 3/2016 | Brown | |
| 9,668,920 B2 | 6/2017 | Akahoshi | |

(Continued)

OTHER PUBLICATIONS

Lin, Hung-Yuan; "A comparison of three different corneal marking methods used to determine cyclotorsion in the horizontal meridian"; Clinical Ophthalmology 2017:11; published Feb. 8, 2017; pp. 311-315.

*Primary Examiner* — Brigid K Byrd
(74) *Attorney, Agent, or Firm* — Mendelsohn Dunleavy, P.C.; Steve Mendelsohn

(57) ABSTRACT

A device for marking a corneal surface of an eye includes a planar base having a central opening, a marking side, and a non-marking side, a linear marker extending across the central opening, and an outer circumference of the planar base having a wall extending vertically away from the non-marking side.

10 Claims, 8 Drawing Sheets

(56) References Cited

U.S. PATENT DOCUMENTS

| | | |
|---|---|---|
| 10,004,642 B1 | 6/2018 | Nallakrishnan et al. |
| 10,786,392 B2 | 9/2020 | Brown |
| 2003/0093083 A1 | 5/2003 | Peyman |
| 2008/0228210 A1* | 9/2008 | Davis .................... A61F 9/0136 606/1 |
| 2009/0254108 A1 | 10/2009 | Davis |
| 2016/0354245 A1 | 12/2016 | Horvath et al. |

* cited by examiner

CORNEAL LINEAR AXIS MARKER

CROSS-REFERENCE TO RELATED APPLICATIONS

This is a continuation of co-pending application Ser. No. 17/384,249, filed on Feb. 23, 2021, the teaching of which are incorporated herein by reference in their entirety.

BACKGROUND

This section provides background information to facilitate a better understanding of the various aspects of the disclosure. It should be understood that the statements in this section of this document are to be read in this light, and not as admissions of prior art.

In the field of refractive cataract surgery there exists a need to place marks on the eye to orient the treatment of astigmatism, among others. In the field of cataract surgery, for example, a corneal astigmatism can be balanced by an intraocular toric lens implant having a curved surface that counterbalances the corneal astigmatism. In such methods for treating astigmatism, the eye should be marked before surgery in order to properly position the treatment of the astigmatism.

SUMMARY

An exemplary device for marking a corneal surface of an eye includes a planar base having a central opening, a marking side, and a non-marking side, a linear marker extending across the central opening, and an outer circumference of the planar base having a wall extending vertically away from the non-marking side.

Another exemplary device for marking a corneal surface of an eye includes a planar base having an inner wall defining a central opening, a top side, and a bottom side, a first passage and a second passage extending vertically through the planar base on opposite sides of the central opening, a linear marker extending across the central opening and positioned above the bottom side, a first end of the linear marker passing through the first passage and tied in a first knot securing the first end to the planar base, a second end of the linear marker passing through the second passage and tied in a second knot securing the second end to the planar base, and an outer circumference of the planar base having a wall extending vertically away from the top side.

This summary is provided to introduce a selection of concepts that are further described below in the detailed description. This summary is not intended to identify key or essential features of the claimed subject matter, nor is it intended to be used as an aid in limiting the scope of claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion. As will be understood by those skilled in the art with the benefit of this disclosure, elements and arrangements of the various figures can be used together and in configurations not specifically illustrated without departing from the scope of this disclosure.

DETAILED DESCRIPTION

Figure 1:
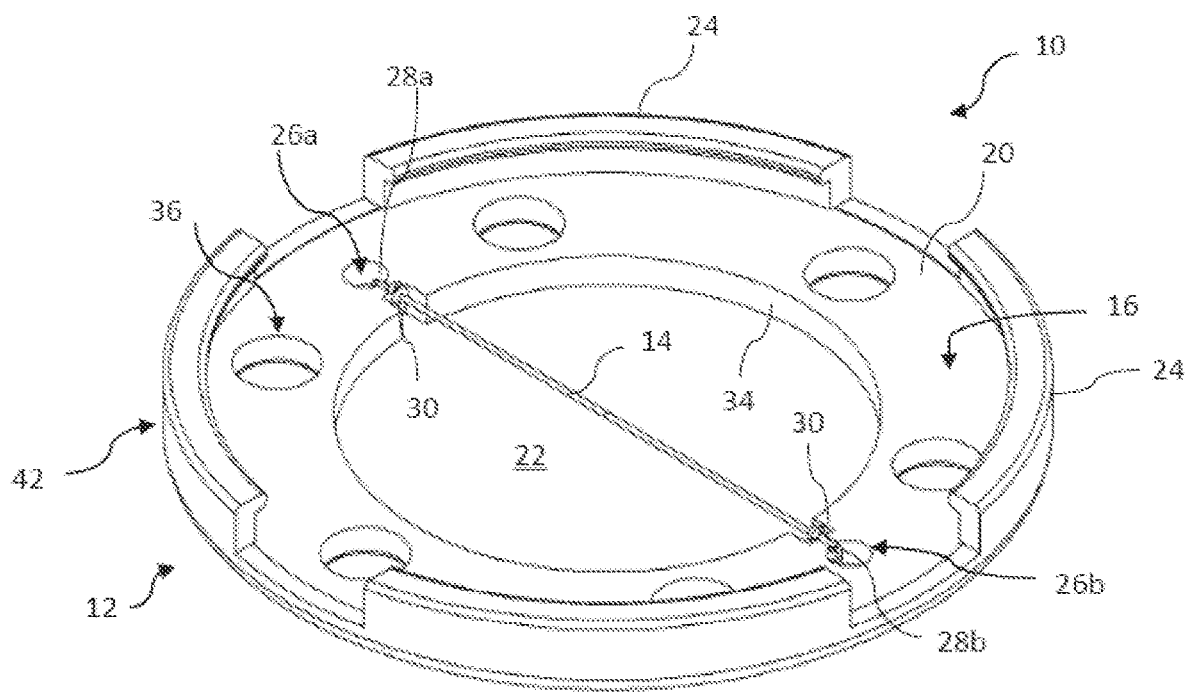
FIG. 1 is a top perspective view of an exemplary corneal linear axis marker.
Figure 2:
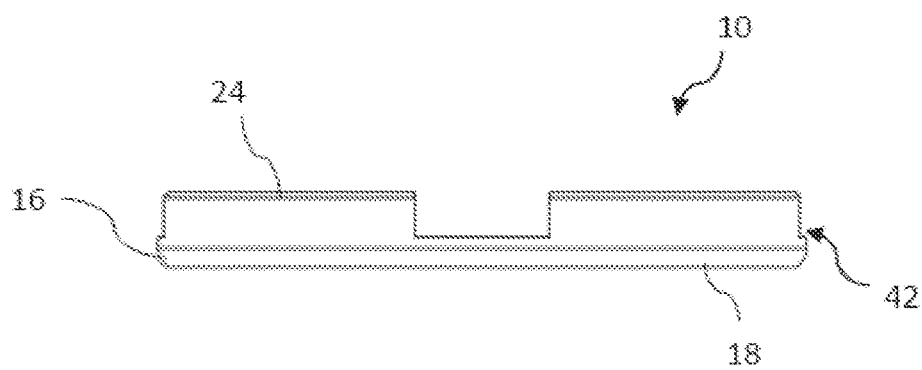
FIG. 2 is an elevation view of the exemplary corneal linear axis marker of FIG. 1.
Figure 3:
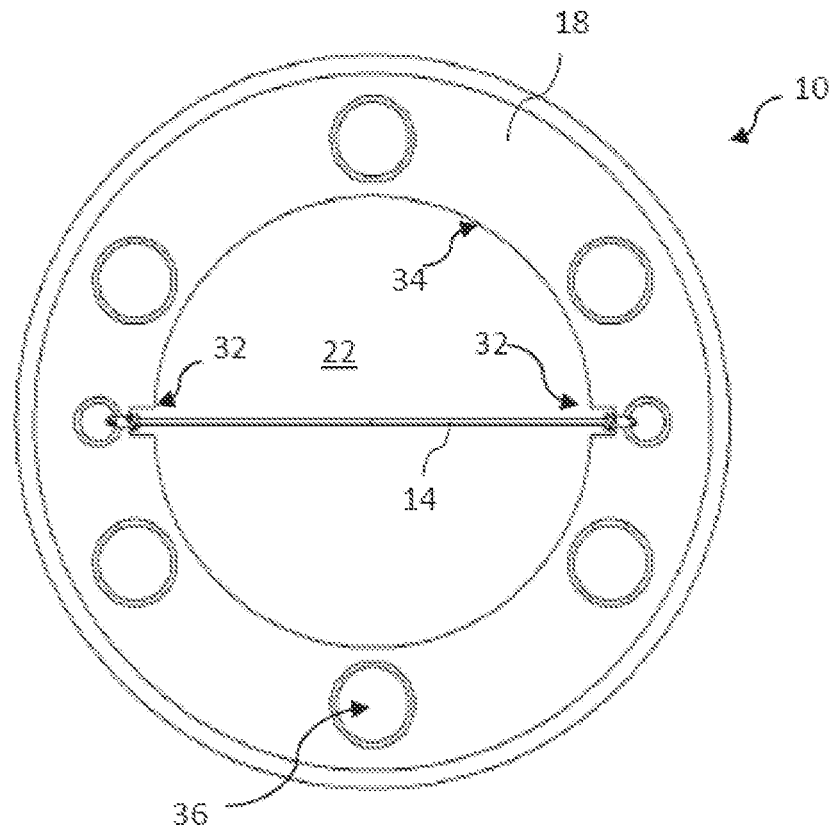
FIG. 3 is a bottom view of the exemplary corneal linear axis marker of FIG. 1.
Figure 4:
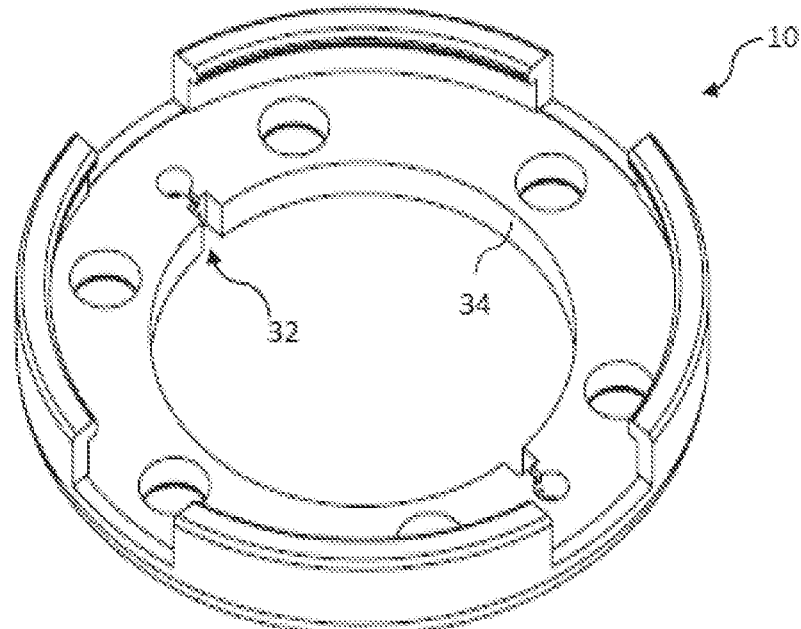
FIG. 4 is a perspective view of the exemplary corneal linear axis marker of FIG. 1 with the marker removed.
Figure 5:
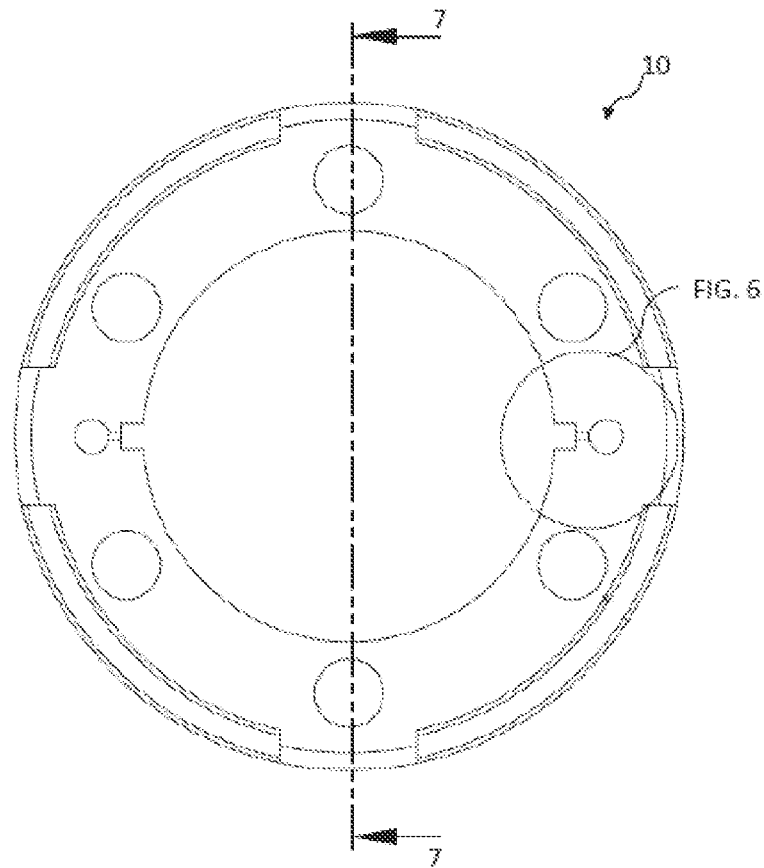
FIG. 5 is a plan view of the exemplary corneal linear axis marker of FIGS. 1 and 4.
Figure 6:
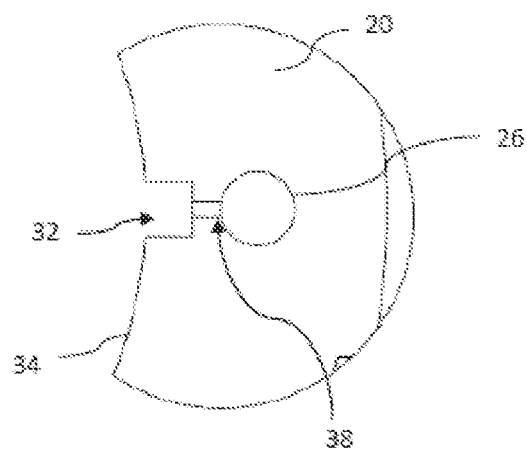
FIG. 6 is an expanded detail view of the section identified in FIG. 5.
Figure 7:
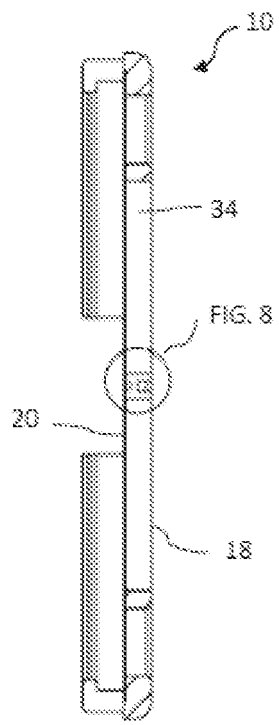
FIG. 7 is a view along the line 7-7 of FIG. 5.
Figure 8:
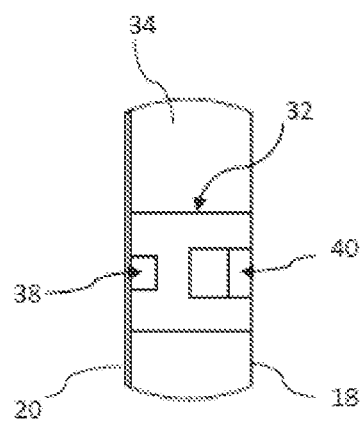
FIG. 8 is an expanded detail view of the section identified in FIG. 7.
Figure 9:
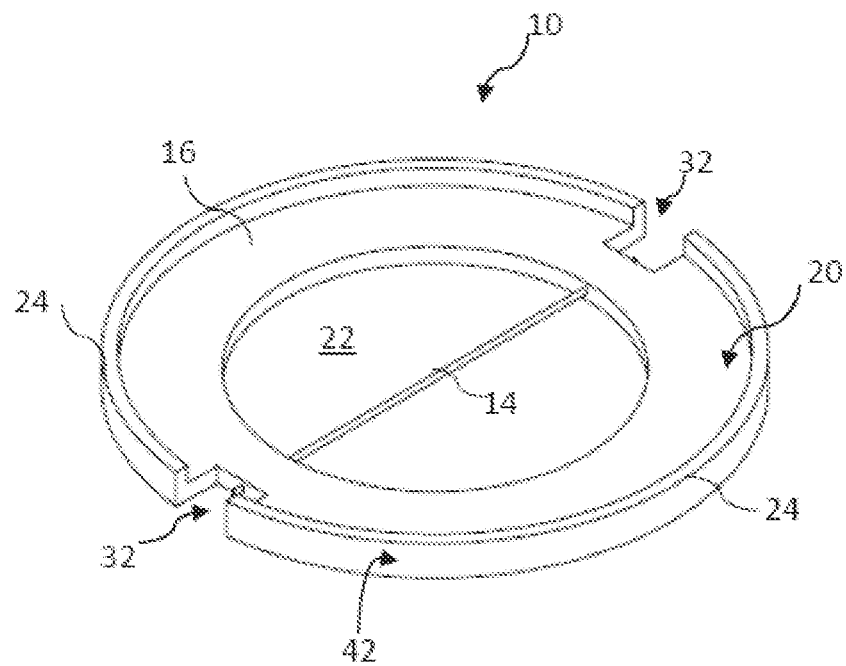
FIG. 9 is a perspective view of another exemplary corneal linear axis marker.
Figure 10:
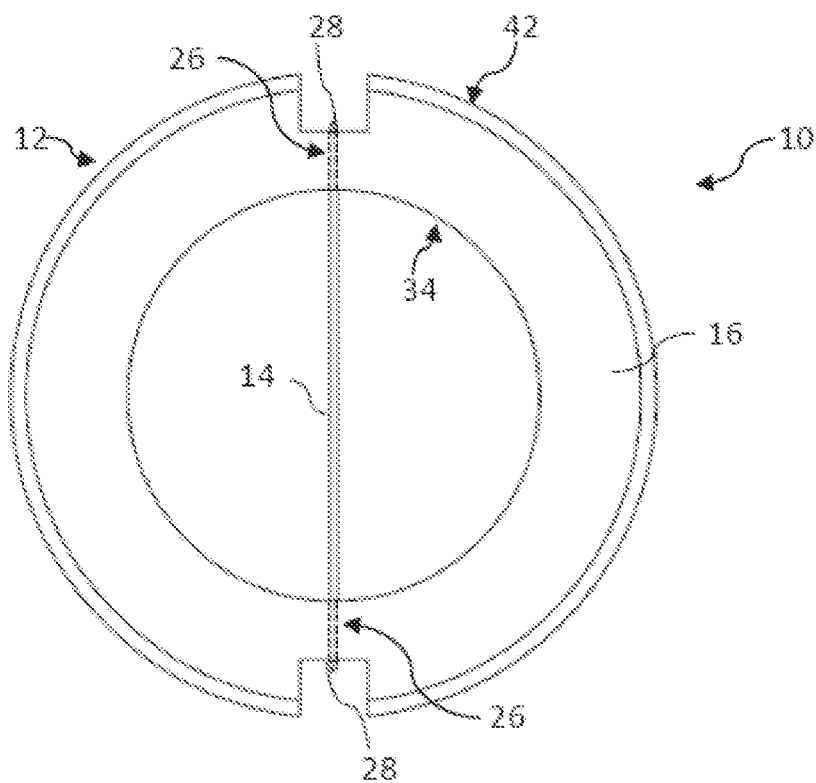
FIG. 10 is a plan view of the exemplary corneal linear axis marker of FIG. 9.
Figure 11:
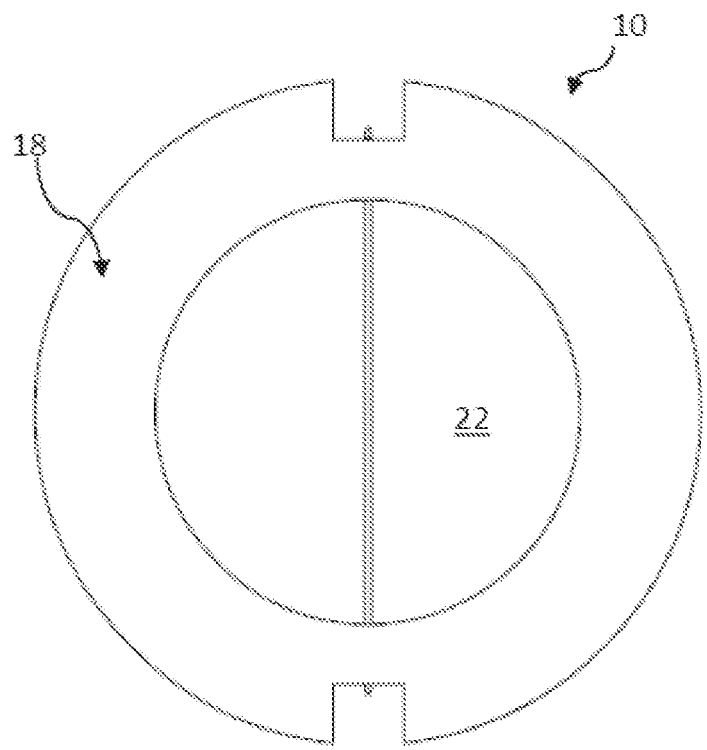
FIG. 11 is a bottom view of the exemplary corneal linear axis marker of FIG. 9.
Figure 12:
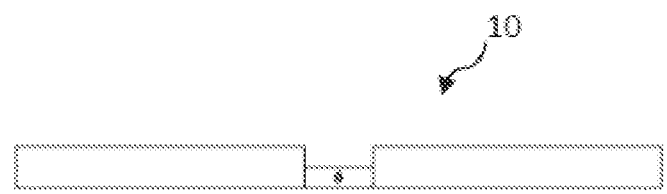
FIG. 12 is an elevation view of the exemplary corneal linear axis marker of FIG. 9.

It is to be understood that the following disclosure provides many different embodiments, or examples, for implementing different features of various illustrative embodiments. Specific examples of components and arrangements are described below to simplify the disclosure. These are, of course, merely examples and are not intended to be limiting. For example, a figure may illustrate an exemplary embodiment with multiple features or combinations of features that are not required in one or more other embodiments and thus a figure may disclose one or more embodiments that have fewer features or a different combination of features than the illustrated embodiment. Embodiments may include some but not all the features illustrated in a figure and some embodiments may combine features illustrated in one figure with features illustrated in another figure. Therefore, combinations of features disclosed in the following detailed description may not be necessary to practice the teachings in the broadest sense and are instead merely to describe particularly representative examples. In addition, the disclosure may repeat reference numerals and/or letters in the various examples. This repetition is for the purpose of simplicity and clarity and does not itself dictate a relationship between the various embodiments and/or configurations discussed.

The corneal linear axis marker ("CLAM") is used to mark a prescribed meridian on the cornea for aligning the axis of an implantable toric intraocular lens used to correct astigmatism. The CLAM is used to create a single linear mark from limbus to limbus and through the central cornea that mirrors the steepest meridian selected for correction. The axis marks on the lens align with the flat meridian of the lens. Aligning the two marks is essential for the best correction. The CLAM creates a linear mark when applied to the cornea by applanation, indentation or transfer of a coloring agent. The CLAM may snap onto any standard degree gauge, such as a Mendez Degree Gauge, and can be rotated to any desired degree marking on the gauge that corresponds to the meridian to be corrected.

FIGS. 1 through 8 illustrate an exemplary embodiment of a CLAM generally denoted by the numeral 10. CLAM 10 comprises a body 12 and a linear marker 14. Body 12 includes a generally planar base 16 having a bottom or marking side 18 and a top or non-marking side 20. Body 12 may be constructed of material including plastics, rubber, and polymers. Base 16 has a central opening 22 configured for placement over a cornea. An exemplary central opening 22 has a diameter of about 12 mm Marker 14 extends axially across central opening 22. Body 12 includes a wall or wall portions 24 extending vertically from non-marking side 20 along the outer circumference 42 of base 16. Vertical is generally perpendicular to planar base 16 and marking side 18. The inside diameter of the wall or wall portions 24 is sized, e.g., about 18 mm, to snap-fit the CLAM onto a degree gauge. Wall or wall portions 24 may be a single structure extending the full circumference of base 16 or two or more portions or sections that may function as tabs to snap-fit, e.g., friction fit, CLAM 10 to a degree gauge. One or more holes 36 may be formed through base 16. The holes 36 may aid in removing CLAM 10 from the degree gauge.

Marker 14 is positioned above marking side 18 to prevent "docking," or premature marking, of the cornea when the CLAM is on the cornea. For example, marker 14 is spaced at least about 100 microns above marking side 18. In the embodiment illustrated in FIGS. 1-8, marker 14 is a length of line attached by tying to base 16 on opposite sides of central opening 22. Marker 14 may be constructed of various materials and with different diameters. The material is flexible in order to conform to the curvature of the cornea. In an exemplary embodiment, marker 14 is constructed of a fluorocarbon or a monofilament, e.g., nylon, fluoropolymer, having a diameter of about 0.13 mm (0.005 inch). In another embodiment, marker 14 may have a diameter in the range of about 0.10 mm to 0.15 mm (0.004-0.006 inch).

Base 16 has a first passage 26a and a second passage 26b positioned 180 degrees apart. In this embodiment, first and second passages 26a, 26b, extend vertically through planar base 16. A first end 28a of marker 14 extends through first passage 26a and is tied to base 16 at first passage 26a. The second end 28b of marker 14 extends through second passage 26b and is tied to base 16 at second passage 26b. In this embodiment, tying marker 14 to base 16 results in knots 30. A channel or recess 32 is formed in the circumference 34 of central opening 22 at each of first and second passages 26a, 26b. Each knot 30 is positioned in a recess 32 and the knot does not extend into central opening 22. In an exemplary embodiment, knots 30 are double half-hitches (two half hitches) positioned toward non-marking side 20. Knots 30 may lift the marker away from marking side 18.

FIGS. 5-8 illustrate an exemplary configuration for tying marker 14 to base 16. Recess 32 is formed in circumferential wall 34 of central opening 22 and terminates before reaching vertical passage 26. Additional recesses, identified as grooves 38, 40 are formed on the respective marking and non-marking sides 18, 20 to dispose the marker. A non-marking side groove 38 is formed in non-marking side 20 and extends from passage 26 to recess 32. For example, non-marking side groove 38 has a depth and a width of about 0.2 mm in a non-limiting embodiment. Marking side groove 40 is formed in marking side 18 and extends from passage 26 to recess 32. Marking side groove 40 has a minimum depth sufficient for marker 14 to be positioned above marking side 18. In a non-limiting example, marking side groove 40 has a depth of about 0.15 mm. The width of marking side groove 40 may be greater than the width of non-marking side groove 38. Marking side groove 40 may have a stepped profile.

FIGS. 9-12 illustrate another exemplary embodiment of a CLAM 10. CLAM 10 includes a body 12 and a linear marker 14. Body 12 includes a generally planar base 16 having a bottom or marking side 18 and a top or non-marking side 20. Base 16 has a central opening 22 configured for placement over a cornea. Marker 14 extends axially across central opening 22. Marker 14 is formed of a flexible line.

Body 12 includes a wall or wall portions 24 extending vertically from non-marking side 20 along the outer circumference 42 of base 16. The inside diameter of the wall or wall portions 24 is sized, e.g., about 18 mm, to snap-fit the CLAM onto a degree gauge. Wall or wall portions 24 may be a single structure extending the full circumference of base 16 or two or more portions or sections that may function as tabs to snap-fit, e.g., friction fit, CLAM 10 to a degree gauge. Base 16 may include vertical holes 36 shown for example in FIG. 1.

Marker 14 extends 180 degrees across central opening 22 and is raised above bottom or marking side 18 to prevent "docking" or premature marking of the cornea. Marker 14 may be a wire or filament. Marker 14 extends through horizontal passages 26 in base 16 with opposing ends 28 secured to base 16 on opposite sides of central opening 22. In this example, opposing recesses 32 are formed 180 degrees from each other in outer circumference 42. Each passage 26 extends horizontally through base 16 from circumference 34 of central opening 22 to recess 32. Horizontal is generally parallel to planar base 16 and marking side 18. Ends 28 of marker 14 are located in the opposed recesses 32. Ends 28 may secure marker 14 to base 16 via various mechanisms including for example tying (knotted), swedged, an adhesive, or melting.

Figure 13:
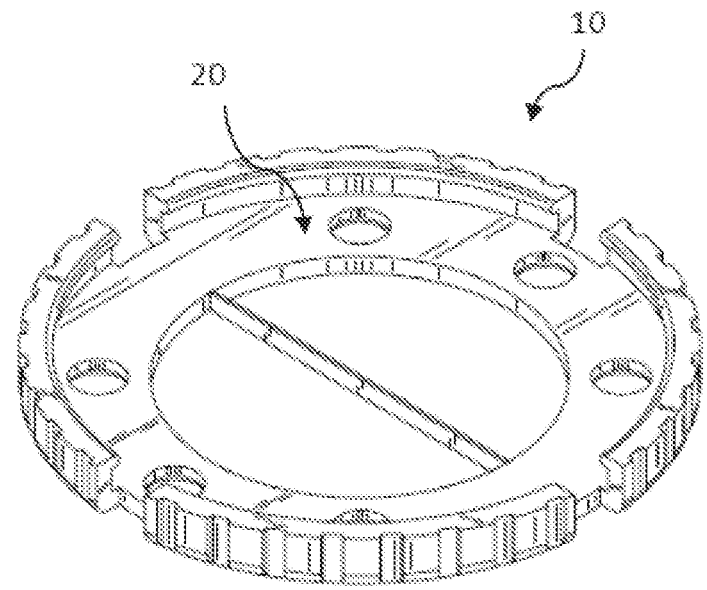
FIG. 13 is a top perspective view of another exemplary corneal linear axis marker.
Figure 14:
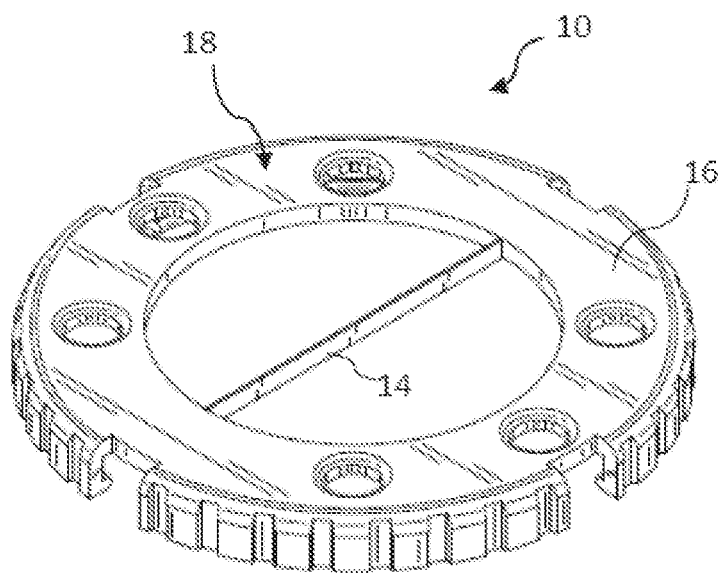
FIG. 14 is a bottom perspective view of the exemplary corneal linear axis marker of FIG. 13.

FIGS. 13-14 illustrate another exemplary embodiment of a CLAM 10. In this example, CLAM 10 is created using additive manufacturing. Marker 14 and base 16 are formed as a unitary structure.

Figure 15:
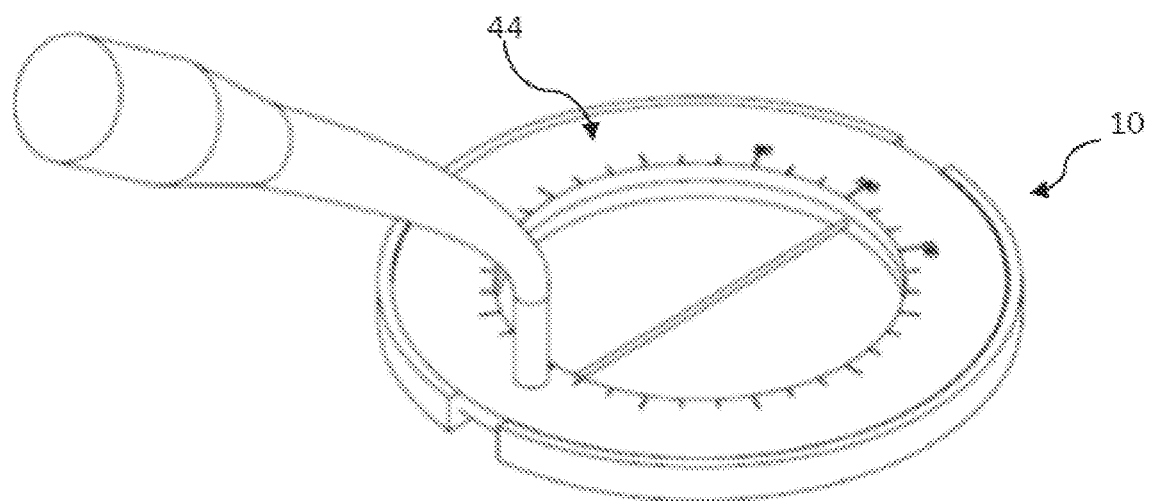
FIG. 15 illustrates an exemplary corneal linear axis marker connected to a degree gauge.

FIG. 15 illustrates an exemplary CLAM 10 mounted on a degree gauge 44.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include such features, elements and/or states. As used herein, the terms "connect," "connection," "connected," "in connection with," and "connecting" may be used to mean in direct connection with or in connection with via one or more elements. Similarly, the terms "couple," "coupling," and "coupled" may be used to mean directly coupled or coupled via one or more elements. Terms such as "up," "down," "top," and "bottom" and other like terms indicating a spatial relationship between various components or to describe the spatial orientation of aspects of such components should be understood to describe a relative relationship between the components or a spatial orientation of aspects of such components.

The term "substantially," "approximately," and "about" is defined as largely but not necessarily wholly what is specified (and includes what is specified; e.g., substantially 90 degrees includes 90 degrees and substantially parallel includes parallel), as understood by a person of ordinary skill in the art. The extent to which the description may vary will depend on how great a change can be instituted and still have a person of ordinary skill in the art recognized the modified feature as still having the required characteristics and capabilities of the unmodified feature. In general, but subject to the preceding, a numerical value herein that is modified by a word of approximation such as "substantially," "approximately," and "about" may vary from the stated value, for example, by 0.1, 0.5, 1, 2, 3, 4, 5, 10, or 15 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an" and other singular terms are intended to include the plural forms thereof unless specifically excluded.

What is claimed is:

1. A device for marking a corneal surface, the device comprising:
    a planar base having a central opening;
    a single marker extending across a single diameter of the central opening and configured to physically contact the corneal surface when the device is pressed over the corneal surface to transfer a linear marking onto the corneal surface consisting of a single line of coloring agent across a single diameter of the corneal surface.

2. The device of claim 1, wherein the single marker is offset at least 100 microns from a marking side of the planar base in the direction of a non-marking side of the planer base.

3. The device of claim 1, wherein the diameter of the central opening is about 12 mm.

4. The device of claim 1, wherein the single marker comprises a single line having opposing ends secured to the planar base.

5. The device of claim 4, wherein the single line is flexible.

6. A method for marking a corneal surface using a device comprising a single marker, the method comprising:
    providing the device with a coloring agent applied to the single marker, wherein the device comprises:
        a planar base having a central opening; and
        the single marker extending across a single diameter of the central opening and configured to physically contact the corneal surface when the device is pressed over the corneal surface;
    aligning the device with respect to the corneal surface;
    pressing the device over the corneal surface such that the single marker physically contacts the corneal surface to transfer a linear marking onto the corneal surface consisting of a single line of the coloring agent across a single diameter of the corneal surface; and
    removing the device from the corneal surface.

7. The method of claim 6, wherein the single marker is offset from a marking side of the planar base in the direction of a non-marking side of the planar base, such that the single marker does not physically contact the corneal surface when aligning the device with respect to the corneal surface.

8. The method of claim 7, wherein the single marker is offset at least 100 microns from the marking side in the direction of the non-marking side.

9. The method of claim 6, wherein the single marker comprises a single line having opposing ends secured to the planar base.

10. The method of claim 9, wherein the single line is flexible.

* * * * *